United States Patent [19]

Clark

[11] Patent Number: 6,090,798
[45] Date of Patent: Jul. 18, 2000

[54] TREATMENT OF GLC1A GLAUCOMA WITH GLUCOCORTICOID ANTAGONISTS

[75] Inventor: Abbot F. Clark, Arlington, Tex.

[73] Assignee: Alcon Laboratories, Inc., Fort Worth, Tex.

[21] Appl. No.: 08/994,233

[22] Filed: Dec. 19, 1997

[51] Int. Cl.[7] ...................................................... A61K 31/56
[52] U.S. Cl. ........................................... 514/178; 514/913
[58] Field of Search ..................................... 514/178, 913

[56] References Cited

U.S. PATENT DOCUMENTS

| | | | |
|---|---|---|---|
| 4,296,206 | 10/1981 | Simons, Jr. | 435/240 |
| 4,753,932 | 6/1988 | Teutsch et al. | 514/179 |
| 4,774,236 | 9/1988 | Cook et al. | 514/176 |
| 4,814,327 | 3/1989 | Ottow et al. | 514/179 |
| 4,829,060 | 5/1989 | Ottow et al. | 514/179 |
| 4,861,763 | 8/1989 | Cook et al. | 514/172 |
| 4,870,069 | 9/1989 | Ottow et al. | 514/179 |
| 4,954,490 | 9/1990 | Cook et al. | 514/176 |
| 5,073,548 | 12/1991 | Cook et al. | 514/169 |
| 5,089,488 | 2/1992 | Ottow et al. | 514/179 |
| 5,089,635 | 2/1992 | Neef et al. | 549/297 |
| 5,093,509 | 3/1992 | Meyer et al. | 556/57 |
| 5,095,129 | 3/1992 | Ottow et al. | 552/510 |
| 5,132,299 | 7/1992 | Ottow et al. | 514/169 |
| 5,166,146 | 11/1992 | Moguilewsky et al. | 514/179 |
| 5,232,915 | 8/1993 | Ottow et al. | 514/63 |
| 5,276,023 | 1/1994 | Moguilewsky et al. | 514/179 |
| 5,426,102 | 6/1995 | Schwede et al. | 514/173 |
| 5,446,178 | 8/1995 | Ottow et al. | 552/510 |
| 5,478,956 | 12/1995 | Ottow et al. | 552/510 |
| 5,519,027 | 5/1996 | Schwede et al. | 514/277 |
| 5,606,043 | 2/1997 | Nguyen et al. | 536/23.5 |

FOREIGN PATENT DOCUMENTS

| | | |
|---|---|---|
| 254670 | of 0000 | European Pat. Off. . |
| 188396 | 7/1986 | European Pat. Off. . |
| 347370 | 12/1989 | European Pat. Off. . |
| 404283 | 12/1990 | European Pat. Off. . |
| 412907 | 2/1991 | European Pat. Off. . |
| 414606 | 2/1991 | European Pat. Off. . |
| 190759 | 8/1986 | Germany . |
| 3619413 | 12/1987 | Germany . |
| 3621024 | 12/1987 | Germany . |
| WO 86/02554 | 5/1986 | WIPO . |
| WO 88/07051 | 9/1988 | WIPO . |
| WO 89/12448 | 12/1989 | WIPO . |
| WO 90/14354 | 11/1990 | WIPO . |
| WO 92/11279 | 7/1992 | WIPO . |
| WO 96/08505 | 3/1996 | WIPO . |

OTHER PUBLICATIONS

"Cellular Mechanisms Influencing the Aqueous Humor Outflow Pathway", Polansky et al, Principles and Practice of Ophtalmology, Jan. 1, 1994, pp. 226–251.

"Steroids, Ocular Hypertension, and Glaucoma", Abbot F. Clark, Ph.D., Journal of Glaucoma, vol. 4, Oct. 1995, pp. 354–369.

Sommer A, et al. Relationship between intraocular pressure and primary open angle glaucoma among white and black Americans. Arch. Ophthalmol. 109:1090–1095, (1991).

Sheffield, et al., "Genetic Linkage of Familial Open Glaucoma to Chromosome 1q21–q31," Nature Genetics, 4:47–50 (1993).

Sarfarazi, et al., "Assignment of a Locus (GLC3A) for Primary Congenital Glaucoma (Buphthalmos) to 2p21 and Evidence for Genetic Heterogeneity," Genomics, 30:171–177 (1995).

Akarsu, et al., "A Second Locus (GLC3B) for Primary Congenital Glaucoma (Buphthalmos) Maps to the 1p36 Region," Human Molecular Genetics, 5(8):1199–1203 (1996).

Stoilova, et al., "Localization of a Locus (GLC1B) for Adult–Onset Primary Open Angle Glaucoma to the 2cen–q13 Region," Genomics, 36:142–150 (1996).

Wirtz, et al., "Mapping a Gene for Adult–Onset Primary Open–Angle Glaucoma to Chromosome 3q," Am. J. Hum. Genet., 60:296–304 (1997).

Andersen, et al., "A Gene Responsible for the Pigment Dispersion Syndrome Maps to Chromosome 7q35–q36," Arch. Ophthalmol., 115:384–388 (1997).

Richards, et al., "Mapping of a Gene for Autosomal Dominant Juvenile–Onset Open–Angle Glaucoma to Chromosome 1q," Am. J. Hum. Genet., 54:62–70 (1994).

Morissette, et al., "A Common Gene for Juvenile and Adult–Onset Primary Open–Angle Glaucomas Confined on Chromosome 1q," Am. J. Hum. Genet., 56:1431–1442 (1995).

Wiggs, et al., "Genetic Linkage of Autosomal Dominant Juvenile Glaucoma to 1q21–q31 in Three Affected Pedigrees," Genomics, 21:299–303 (1994).

Meyer, et al., "Age–Dependent Penetrance and Mapping of the Locus for Juvenile and Early–Onset Open–Angle Glaucoma on Chromosome 1q (GLC1A) in a French Family," Hum. Genet., 98:567–571 (1996).

Graff, et al., "Confirmation of Linkage to 1q21–31 in a Danish Autosomal Dominant Juvenile–Onset Glaucoma Family and Evidence of Genetic Heterogeneity," Hum. Genet., 96:285–289 (1995).

Stone, et al., "Identification of a Gene That Causes Primary Open Angle Glaucoma," Science, 275:668–670 (1997).

Polansky, et al., "Eicosanoid Production and Glucocorticoid Regulatory Mechanisms in Cultured Human Trabecular Meshwork Cells," The Ocular Effects of Prostaglandins and Other Eicosanoids, pp. 113–138 (1989).

Polansky, et al., "In Vitro Correlates of Glucocorticoid Effects on Intraocular Pressure," Glaucoma Update IV (1991).

(List continued on next page.)

*Primary Examiner*—Zohreh Fay
*Attorney, Agent, or Firm*—Sally Yeager

[57] ABSTRACT

Compositions of glucocorticoid antagonists for treating mammals suffering from GLC1A glaucoma and methods for their use are disclosed.

3 Claims, No Drawings

OTHER PUBLICATIONS

Polansky, et al., "Cellular Pharmacology and Molecular Biology of the Trabecular Meshwork Inducible Glucocorticoid Response Gene Product," Ophthalmologica, 211:126–139 (1997).

Ortego, et al., "Cloning and Characterization of Subtracted cDNAs from a Human Ciliary Body Library Encoding TIGR, a Protein Involved in Juvenile Open Angle Glaucoma with Homology to Myosin and Olfactomedin," FEBS Letters, 413:349–353 (1997).

(Kubota, et al., "A Novel Myosin–like Protein (Myocilin) Expressed in the Connecting Cilium of the Photoreceptor: Molecular Cloning, Tissue Expression, and Chromosomal Mapping," Genomics, 41:360–369 (1997).

Sunden, et al., "Fine Mapping of the Autosomal Dominant Juvenile Open Angle Glaucoma (GLC1A) Region and Evaluation of Candidate Genes," Genome Research, 6:862–869 (1996).

Adam, et al., "Recurrent Mutations in a Single Exon Encoding the Evolutionarily Conserved Olfactomedin–Homology Domain of TIGR in Familial Open–Angle Glaucoma," Human Molecular Genetics, 6(12):2091–2097 (1997).

Kass, et al., "Corticosteroid–Induced Glaucoma, In Ritch, R., Shields, M. B., Krupin, T. (eds.)," The Glaucomas, The C. V. Mosby Company, St. Louis, MO, pp. 1161–1168 (1989).

DeSantis, et al., Dexamethasone–Induction of Ocular Hypertension in the Primate, ARVO Abstracts. Invest. Ophthalmol. Vis. Sci., 31(Suppl.):99 (1990).

Knepper, et al., "Intraocular Pressure and Glycosaminoglycan Distribution in the Rabbit Eye: Effect of Age and Dexamethasone," Exp. Eye Res., 27:567–575 (1978).

Francois, et al., Ultrastructural and Morphometric Study of Corticosteroid Glaucoma in Rabbits, Ophthalmic Res., 16:168–178 (1984).

Lorenzetti, O. J., "Effects of Corticosteroids on Ocular Dynamics in Rabbits," J. Pharmacol. Exp. Therap., 175:763–772 (1970).

Zhan, et al., "Steroid Glaucoma: Corticosteroid–Induced Ocular Hypertension in Cats," Exp. Eye Res., 54:211–218 (1992).

Rozsival, et al., "Aqueous Humour and Plasma Cortisol Levels in Glaucoma and Cataract Patients," Current Eye Research, 1:391–396 (1981).

Ray, et al., "Plasma Cortisol in Glaucoma," Ann. Ophthalmol., 9:1151–1154 (1977).

Schwartz, et al., "Increased Plasma Free Cortisol in Ocular Hypertension and Open Angle Glaucoma," Arch. Ophthalmol., 105:1060–1065 (1987).

Wilson, et al., Dexamethasone Induced Ultrastructural Changes in Cultured Human Trabecular Meshwork Cells, Cur. Eye Res., 12:783–793 (1993).

Clark, et al., "Glucocorticoid–Induced Formation of Cross–Linked Actin Networks in Cultured Human Trabecular Meshwork Cells," Invest. Ophthalmol. Vis. Sci., 35:281–294 (1994).

(Green, et al., "Ocular Fluid Dynamics Response to Topical RU486, a Steroid Blocker," Current Eye Research, 4:605–612 (1985).

Tsukahara, et al., "Subconjunctival Suspension of RU486 Lowers Intraocular Pressure in Normal Rabbits," Br. J. Ophthalmol., 70:451–455 (1986).

Denis, et al., "Mifepristone (RU486): In Vitro Binding to Glucocorticoid Receptors in Iris–Cillary Body and In Vivo Effects on Intraocular Pressure in Rabbits," Invest. Ophthalmol. Vis. Sci., 34[Suppl.]:1115 (1993).

TREATMENT OF GLC1A GLAUCOMA WITH GLUCOCORTICOID ANTAGONISTS

This application is directed to the use of glucocorticoid antagonists for treating glaucoma or ocular hypertension resulting from altered expression of the GLC1A gene (hereinafter GLC1A or 1q glaucoma) in an individual.

BACKGROUND OF THE INVENTION

The glaucomas are a heterogeneous group of optic neuropathies characterized by cupping of the optic nerve head, thinning of the retinal nerve fiber layer due to loss of retinal ganglion cells, and specific pathognomonic changes in visual fields. Elevated intraocular pressure (IOP) is a very important risk factor for the development of most common forms of glaucoma (Sommer A, et al., "Relationship Between Intraocular Pressure and Primary Open Angle Glaucoma Among White and Black Americans," *Arch. Ophthalmol.*, 109:1090–1095 (1991).

A family history of glaucoma also is an important risk factor for the development of glaucoma. It appears that a significant portion of glaucoma is inherited (or at least the risk for developing glaucoma is inherited) although it is often difficult to establish clear inheritance patterns for most of the glaucomas because of the disease onset late in life and the slowly progressive clinical manifestations of the disease. Despite these problems, a number of families with heritable forms of glaucoma have been identified and these families have been used to map a variety of glaucoma genes (Sheffield, et al., "Genetic Linkage of Familial Open Angle Glaucoma to Chromosome 1q21-q31," *Nature Genetics*, 4:47–50 (1993); Sarfarazi, et al., "Assignment of a Locus (GLC3A) for Primary Congenital Glaucoma (Buphthalmos) to 2p21 and Evidence for Genetic Heterogeneity," *Genomics*, 30:171–177 (1995); Akarsu, et al., "A Second Locus (GLC3B) for Primary Congenital Glaucoma (Buphthalmos) Maps to the 1p36 Region," *Human Molecular Genetics*, 5(8):1199–1203 (1996); Stoilova, et al., "Localization of a Locus (GLC1B) for Adult-Onset Primary Open Angle Glaucoma to the 2cen-q13 Region," *Genomics*, 36:142–150 (1996); Wirtz, et al., "Mapping a Gene for Adult-Onset Primary Open-Angle Glaucoma to Chromosome 3q," *Am. J Hum. Genet.*, 60:296–304 (1997); Andersen, et al., "A Gene Responsible for the Pigment Dispersion Syndrome Maps to Chromosome 7q35-q36," *Arch. Ophthalmol*, 115:384–388 (1997)). The first glaucoma gene mapped (GLC1A) was in a large family with autosomal dominant inherited juvenile glaucoma (JG). This disease is characterized by an early disease onset (late teens to early 20s), relatively high IOPs, and general resistance to conventional pharmacological IOP lowering therapy. The GLC1A gene was mapped by positional cloning and linkage analysis to chromosome 1q22-q25 (Sheffield et al, Id.) and a number of other groups have confirmed the 1q location of this juvenile glaucoma gene (Richards, et al., "Mapping of a Gene for Autosomal Dominant Juvenile-Onset Open-Angle Glaucoma to Chromosome 1q," *Am. J Hum. Genet.*, 54:62–70 (1994); Morissette, et al., "A Common Gene for Juvenile and Adult-Onset Primary Open-Angle Glaucomas Confined on Chromosome 1q," *Am. J Hum. Genet.*, 56:1431–1442 (1995); Wiggs, et al., "Genetic Linkage of Autosomal Dominant Juvenile Glaucoma to 1q21-q31 in Three Affected Pedigrees," *Genomics*, 21:299–303 (1994); Meyer, et al., "Age-Dependent Penetrance and Mapping of the Locus for Juvenile and Early-Onset Open-Angle Glaucoma on Chromosome 1q (GLC1A) in a French Family," *Hum. Genet.*, 98:567–571 (1996); Graff, et al., "Confirmation of Linkage to 1q21-31 in a Danish Autosomal Dominant Juvenile-Onset Glaucoma Family and Evidence of Genetic Heterogeneity," *Hum. Genet.*, 96:285–289 (1995)). Glaucoma due to the GLC1A gene is often referred to as 1q glaucoma.

The GLC1A gene was identified as encoding a 57 kD protein expressed in the trabecular meshwork (TM) (Stone, et al., "Identification of a Gene That Causes Primary Open Angle Glaucoma," *Science*, 275:668–670 (1997)). The expression of the GLC1A gene, and the encoded TM protein, is up-regulated by glucocorticoids (Polansky, et al., "Eicosanoid Production and Glucocorticoid Regulatory Mechanisms in Cultured Human Trabecular Meshwork Cells," *The Ocular Effects of Prostaglandins and Other Eicosanoids*, pp. 113–138 (1989); Polansky, et al., "In Vitro Correlates of Glucocorticoid Effects on Intraocular Pressure," *Glaucoma Update IV* (1991); and Polansky, et al., "Cellular Pharmacology and Molecular Biology of the Trabecular Meshwork Inducible Glucocorticoid Response Gene Product," *Ophthalmologica*, 211:126–139 (1997)). This TM protein is also known as TIGR (trabecular meshwork inducible glucocorticoid response) (Polansky, Id.). The glucocorticoid-induction of this TM protein has been suggested to be involved in the generation of glucocorticoid-induced ocular hypertension and glaucoma (Polansky, Id.).

The GLC1A gene is expressed in other ocular tissues such as the ciliary epithelium (Ortego, et al., "Cloning and Characterization of Subtracted cDNAs from a Human Ciliary Body Library Encoding TIGR, a Protein Involved in Juvenile Open Angle Glaucoma with Homology to Myosin and Olfactomedin," *FEBS Letters*, 413:349–353 (1997)) and the retina (Kubota, et al., "A Novel Myosin-like Protein (Myocilin) Expressed in the Connecting Cilium of the Photoreceptor: Molecular Cloning, Tissue Expression, and Chromosomal Mapping," *Genomics*, 41:360–369 (1997)). The gene is referred to by several names including GLC1A (Sheffield, supra; Sunden, et al., "Fine Mapping of the Autosomal Dominant Juvenile Open Angle Glaucoma (GLC1A) Region and Evaluation of Candidate Genes," *Genome Research*, 6:862–869 (1996); Stone, et al., supra), TIGR (Polansky supra; Ortego, supra), and myocilin (Kubota, supra). Mutations GLC1A are not only responsible for juvenile glaucoma, but also a significant subset of adult onset primary open angle glaucoma (Stone, et. al., supra; Adam, et al., "Recurrent Mutations in a Single Exon Encoding the Evolutionarily Conserved Olfactomedin-Homology Domain of TIGR in Familial Open-Angle Glaucoma," *Human Molecular Genetics*, 6(12):2091–2097 (1997)). The 1q glaucoma gene (GLC1A, TIGR) is the subject of Nguyen, et al., U.S. Pat. No. 5,606,043, issued Feb. 25, 1997.

Glaucomatous damage to vision is usually related to elevated IOP in a pressure sensitive eye. In glaucoma the trabecular meshwork (TM) of the eye is damaged causing increased aqueous humor outflow resistance resulting in elevated IOP. Glucocorticoids have been associated with the development of ocular hypertension and primary open angle glaucoma (Kass, et al., "Corticosteroid-Induced Glaucoma, In Ritch, R., Shields, M. B., Krupin, T. (eds.)," *The Glaucomas*, The C. V. Mosby Company, St. Louis, Mo., pp. 1161–1168 (1989); DeSantis, et al., "Dexamethasone-Induction of Ocular Hypertension in the Primate," *ARVO Abstracts. Invest. Ophthalmol. Vis. Sci.*, 31(Suppl.): 99 (1990); Knepper, et al., "Intraocular Pressure and Glycosaminoglycan Distribution in the Rabbit Eye: Effect of Age and Dexamethasone," *Exp. Eye Res.*, 27:567–575 (1978); Francois, et al., "Ultrastructural and Morphometric Study of Corticosteroid Glaucoma in Rabbits," *Ophthalmic Res.*, 16:168–178 (1984); Lorenzetti, O. J., "Effects of Corticosteroids on Ocular Dynamics in Rabbits," *J. Pharmacol. Exp. Therap.*, 175:763–772 (1970); and Zhan, et al., "Steroid Glaucoma: Corticosteroid-Induced Ocular Hypertension in Cats," *Exp. Eye Res.*, 54:211–218 (1992)). Glaucoma patients have also been reported to have higher levels of the endogenous glucocorticoid, cortisol (Rozsival, et al., "Aqueous Humour and Plasma Cortisol Levels in Glaucoma and Cataract Patients," *Current Eye Research*, 1:391–396

(1981); Ray, et al., "Plasma Cortisol in Glaucoma," *Ann. Ophthalmol.*, 9:1151–1154 (1977); and Schwartz, et al., "Increased Plasma Free Cortisol in Ocular Hypertension and Open Angle Glaucoma," *Arch. Ophthalmol.*, 105:1060–1065 (1987)).

It is known that trabecular meshwork cells have glucocorticoid receptors and that glucocorticoid binding with these receptors causes a change in trabecular meshwork cell gene expression. Known manifestations of this change include a reorganization of the cytoskeleton (Wilson, et al., "Dexamethasone Induced Ultrastructural Changes in Cultured Human Trabecular Meshwork Cells," *Cur. Eye Res.*, 12:783–793 (1993) and Clark, et al., "Glucocorticoid-Induced Formation of Cross-Linked Actin Networks in Cultured Human Trabecular Meshwork Cells," *Invest. Ophthalmol. Vis. Sci.*, 35:281–294 (1994)) and increased deposition of the extracellular matrix material in trabecular meshwork cells. As a result, the trabecular meshwork becomes "clogged" and unable to perform one of its most critical functions, that is, serving as a gateway for aqueous humor flow from the anterior chamber of the eye. When the aqueous humor flow out of the eye via the trabecular meshwork is diminished, the intraocular pressure of the eye rises. If this state of elevated intraocular pressure is maintained or frequently occurs, the optic nerve head can be damaged resulting in the loss of visual field. Loss of visual field is the hallmark symptom associated with glaucoma.

Knepper, et al. (WO 86/02554) disclose the use of selected anabolic androgenic compounds for treating glaucoma.

Endogenous glucocorticoids may be responsible for producing the changes in the trabecular meshwork that lead to ocular hypertension and glaucoma. In the present case, it is believed that glucocorticoid antagonists bind to tie glucocorticoid receptor in trabecular meshwork cells, and thereby prevent binding of endogenous glucocorticoids to the glucocorticoid receptor. They may also displace endogenous glucocorticoids which are bound to glucocorticoid receptors.

The glucocorticoid antagonist RU486 has been reported to lower IOP in normotensive rabbits (Green, et al., "Ocular Fluid Dynamics Response to Topical RU486, a Steroid Blocker," *Current Eye Research*, 4:605–612 (1985); Tsukahara, et al., "Subconjunctival Suspension of RU486 Lowers Intraocular Pressure in Normal Rabbits," *Br. J. Ophthalmol.*, 70:451–455 (1986)) and in rabbits with glucocorticoid-induced ocular hypertension (Denis, et al., "Mifepristone (RU486): In Vitro Binding to Glucocorticoid Receptors in Iris-Ciliary Body and In Vivo Effects on Intraocular Pressure in Rabbits," *Invest. Ophthalmol. Vis. Sci.*, 34[Suppl.]:1115 (1993)).

In summary, the GLC1A gene product can lead to the development of ocular hypertension and glaucoma in one of two ways: (1) mutations in GLC1A are responsible for most forms of juvenile glaucoma and a subset of adult onset POAG or (2) exposure of some individuals to glucocorticoids leads to increased GLC1A expression in the TM which causes increased aqueous humor outflow resistance and the development of ocular hypertension. The precise mechanism(s) responsible for GLC1A effects on IOP are currently unknown.

SUMMARY OF THE INVENTION

Glucocorticoid antagonists (GAs) and their pharmaceutical formulations are useful for treating persons with GLC1A glaucoma. The invention is also directed to methods for controlling GLC1A glaucoma using GAs.

DESCRIPTION OF THE PREFERRED EMBODIMENTS

Agents which alter the expression of GLC1A in the glaucomatous eye are expected to lower IOP and thereby prevent or inhibit the glaucomatous optic neuropathy which is being driven by elevated IOP. Glucocorticoids upregulate GLC1A expression in the TM of certain individuals. There have been several reports of elevated levels of the natural glucocorticoid cortisol in the aqueous humor and plasma of glaucoma patients (Schwartz, et al., supra; Rozsival, et al., supra). In addition, certain mutations in GLC1A may alter the expression of GLC1A in the TM tissue of 1q glaucoma patients. Unexpectedly, it has been discovered that certain glucocorticoid antagonists (GA) inhibit the expression of GLC1A in cultured human TM cells and lower elevated IOP in certain animal models of ocular hypertension. The GAs appear to work by inhibiting glucocorticoids from binding to the glucocorticoid receptor. The GAs thereby prevent the expression of GLC1A and the subsequent development of ocular hypertension.

As used herein the term glucocorticoid antagonist refers to a compound which binds to the glucocorticoid receptor and prevents receptor activation.

GAs which are particularly useful for treating persons with GLC1A glaucoma include the following compounds:

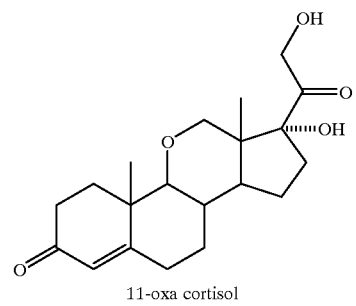

11-oxa cortisol

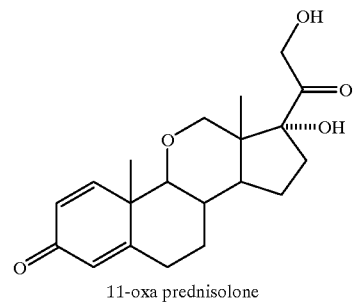

11-oxa prednisolone

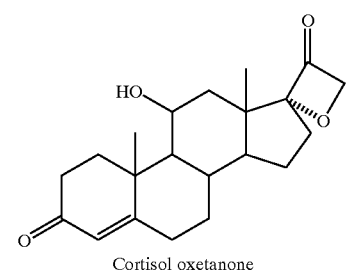

Cortisol oxetanone

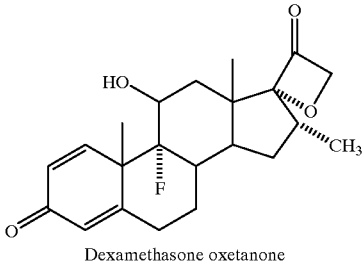

Dexamethasone oxetanone

-continued

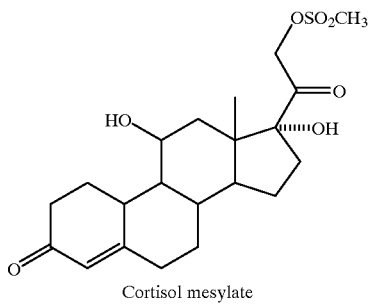
Cortisol mesylate

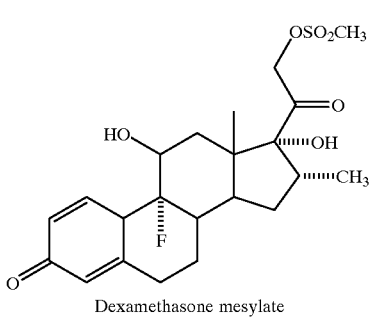
Dexamethasone mesylate

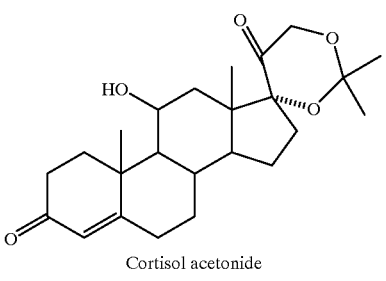
Cortisol acetonide

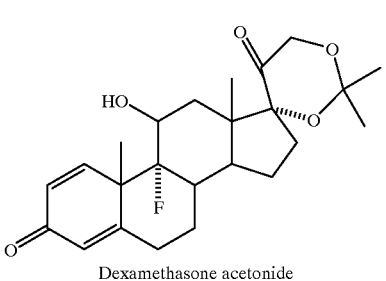
Dexamethasone acetonide

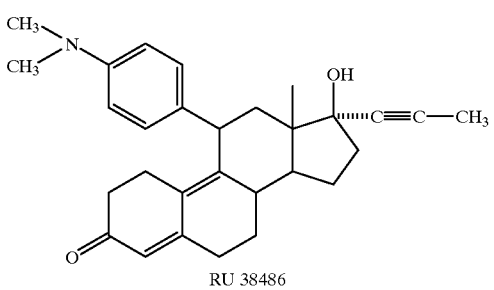
RU 38486

-continued

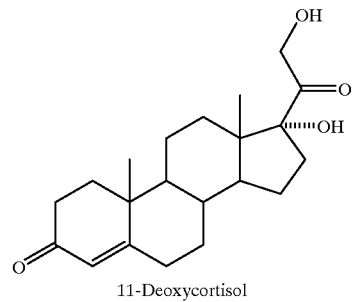
11-Deoxycortisol

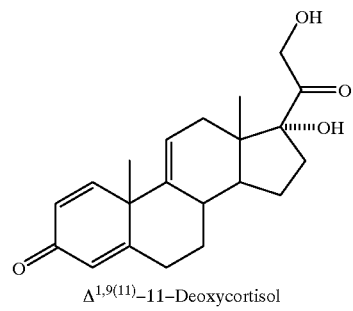
$\Delta^{1,9(11)}$-11-Deoxycortisol

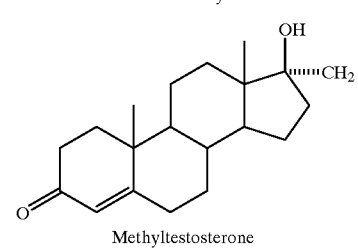
Methyltestosterone

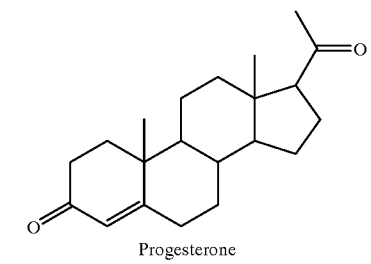
Progesterone

Additional glucocorticoid antagonists which are useful according to the present invention can be found in the following patents and patent applications which are incorporated herein by reference: U.S. Pat. Nos. 5,073,548; 4,954,490; 4,861,763; 4,774,236; 5,276,023; 5,166,146; 4,753,932; 5,519,027; 5,478,956; 5,446,178; 5,426,102; 5,232,915; 5,132,299; 5,095,129; 5,093,509; 5,089,635; 5,089,488; 4,870,069; 4,829,060; and 4,814,327; WO 89/12448; WO 96/08505; WO 92/11279; WO 90/14354; WO 88/07051; EP 412907 A; EP 414606 A; EP 188396 A; EP 404283; EP 347370; EP 254670 A; EP 190759 A; DE 3621024 A; and DE 3619413 A.

Topical formulation s contain about 0.05 to 5 wt. % of a glucocorticoid antagonist. Systemic formulations contain about 10 to 1000 mg.

The formulations can be administered systemically or topically, preferably topically, one to four times daily according to the discretion of a skilled clinician.

The following examples are not meant to be limiting.

EXAMPLE 1

Topical Ocular Formulation of Glucocorticoid Antagonist.

| Ingredient | Amount (wt. %) |
|---|---|
| Glucocorticoid Antagonist | 1.0 |
| Mannitol | 2.40 |
| Sodium Chloride | 0.40 |
| Carbopol 974P | 0.50 |
| Polysorbate 80 | 0.05 |
| Edetate Sodium | 0.01 |
| Benzalkonium Chloride | 0.01 |
| Sodium Hydroxide | Adjust pH to 7.2 |
| Purified Water | qs to 100% |

EXAMPLE 2

Formulation for Oral Administration.

Tablet: 10–1000 mg of glucocorticoid antagonist with inactive ingredients such as cornstarch, lactose, colloidal silicon dioxide, microcrystalline cellulose, and magnesium stearate can be formulated according to procedures known to those skilled in the art of tablet formulation.

I claim:

1. A method for treating GLC1A glaucoma which comprises administering a pharmaceutically effective amount of a glucocorticoid antagonist.

2. The method of claim 1 wherein the glucocorticoid antagonist is selected from the group consisting of RU486, 11-oxa cortisol, 11-oxa prednisolone, cortisol oxetanone, dexamethasone oxetanone, cortisol mesylate, dexamethasone mesylate, cortisol acetonide, dexamethasone acetonide, 11-deoxycortisol, $\Delta^{1,9(11)}$-11-deoxycortisol, methyltestosterone, and progesterone.

3. The method of claim 1 wherein the glucocorticoid antagonist is RU486.

* * * * *